United States Patent [19]

Fock et al.

[11] Patent Number: 5,447,981
[45] Date of Patent: Sep. 5, 1995

[54] (METH) ACRYLIC ACID POLYMER DISPERSION

[75] Inventors: Jürgen Fock, Düsseldorf; Götz Koerner, Essen; Karl-Heinz Reichert, Berlin; Stephan Fengler, Berlin; Roland Smolin, Berlin, all of Germany

[73] Assignee: Th. Goldschmidt AG, Essen, Germany

[21] Appl. No.: 225,217

[22] Filed: Apr. 8, 1994

[30] Foreign Application Priority Data

Apr. 10, 1993 [DE] Germany .................. 43 11 916.6

[51] Int. Cl.⁶ ..................... C08F 2/16; C08K 3/20
[52] U.S. Cl. ..................... 524/458; 524/457; 524/461; 524/505
[58] Field of Search ............... 524/457, 458, 461, 505

[56] References Cited

U.S. PATENT DOCUMENTS

| | | | |
|---|---|---|---|
| 3,284,393 | 11/1966 | Wiley | 260/29.6 |
| 3,950,284 | 4/1976 | Fukuda et al. | 524/461 |
| 4,147,688 | 4/1979 | Makhlouf et al. | 524/461 |
| 4,616,058 | 10/1986 | Yabata et al. | 524/461 |
| 4,798,691 | 1/1989 | Kasai et al. | 524/461 X |
| 5,262,455 | 11/1993 | Riess et al. | 524/505 X |

FOREIGN PATENT DOCUMENTS 2140433  4/1984  European Pat. Off. .
4134967  12/1992  Germany .

OTHER PUBLICATIONS

Prof. Dr. H. G. Kilian, Colloid & Polymer Science, 1986, 4(pgs).
par Yee Sing Leong, Polymerisation D'acrylamide . . . , Nov. 12, 1980, 6(pgs).

Primary Examiner—Judy M. Reddick
Attorney, Agent, or Firm—Anderson Kill Olick & Oshinsky

[57] ABSTRACT

A poly(meth) acrylic acid dispersion with an organic solvent as outer phase, the dispersed phase particles having a low polydispersity is obtained by the free radical polymerization of (meth) acrylic acid and optionally co-monomers, which bring about a cross-linking of the poly(meth) acrylic acid, in a nonpolar, organic solvent in the presence of stabilizers, costabilizers, and initiators. The stabilizer is a block copolymer.

11 Claims, No Drawings

(METH) ACRYLIC ACID POLYMER DISPERSION

FIELD OF INVENTION

The invention relates to a poly(meth)acrylic acid dispersion with an organic solvent as outer phase, the dispersed phase particles having an average particle size of about 20 to 300 nm and a low polydispersity.

BACKGROUND INFORMATION AND PRIOR ART

The polymerization of monomers, which contain acrylic groups, in the form of water-in-oil emulsion, is known from the prior art. Dispersions are obtained, the particle size of which generally is larger than 300 nm. At the same time, the particles have a relatively broad spectrum of particle sizes.

The following publications are referred to as being representative of the extensive prior art:

In the "Journal de chimie physique", 1981, volume 78, number 3, Y. S. Leong, G. Riess and F. Candau, using an oil-soluble free radical-forming material, report the photopolymerization of acrylamide into a water-in-oil emulsion. The reaction is carried out in the presence of a polystyrene-polyoxyalkylene block copolymer as stabilizer and propanol in toluene-water mixtures. The latexes obtained are transparent and, as confirmed by dialysis experiments, consist of micellar solutions swollen in water. The molecular weight of the polyacrylamide obtained falls within the range of 50,000 to 130,000.

From the "Colloid Polym. Sci.", 264 (7), 616, the synthesis of poly(vinyl acetate) and poly(methyl methacrylate) in the form of particles with a diameter of 100 to 300 nm is known by the dispersion polymerization in a nonaqueous medium in the presence of polystyrene-polyoxyalkylene copolymers. For this synthesis, the particle diameter decreases as the concentration of block copolymer increases.

The British patent 2,140,433 discloses the preparation of stable water-in-oil emulsions with a high polymer content and a low viscosity by a free radical polymerization by the addition of the aqueous solution of a water-soluble monomer, such as acrylic acid, to an inert, hydrophobic, organic liquid.

U.S. Pat. No. 3,284,393 relates to a method, in which water-soluble monomers, such as acrylic acid, methacrylic acid, acrylamide and other monomers in aqueous solution are emulsified in a water-immiscible oil in the presence of a low molecular weight emulsifier, such as sorbitol monooleate, and a buffer. The polymerization is carried out with oil-soluble free radical initiators. Polymer particles with a diameter of about 100 nm are obtained at a reaction temperature of 60° C. in the course of a reaction requiring 48 hours for completion.

OBJECT OF THE INVENTION

An object of the present invention is poly(meth)acrylic acid dispersion with an organic solvent as outer phase, so that the dispersed phase particles have a significantly smaller particle size of about 20 to 300 nm and, additionally, that the polydispersity of the particles, that is, the scatter of their particle sizes, is as small as possible. The method shall proceed easily, in yields as quantitative as possible and within economically justifiable polymerization times. The dispersions obtained have a high stability.

SUMMARY OF THE INVENTION

Pursuant to the present invention, such poly(meth)acrylic acid dispersions, with an organic solvent as outer phase, the dispersed phase particles having an average particle size of 20 to 300 nm and a low polydispersity, can be obtained by the free radical polymerization of (meth)acrylic acid and optionally up to 5% by weight of co-monomers, which bring about a cross-linking of the poly(meth)acrylic acid, in a nonpolar, organic solvent in the presence of stabilizers, costabilizers and initiators, wherein (1) the stabilizer is a block copolymer, which consists of at least one block A and at least one block B, block A being formed by the polymerization of monomers containing vinyl groups and block B being a polyoxyalkylene block, (2) the ratio by weight of the stabilizer to the sum of the (meth)acrylic acid and co-monomers optionally contained is 1:3 to 1:100, (3) the costabilizer is water or a dihydric alcohol with up to 3 carbon atoms, and (4) the ratio by weight of costabilizer to the sum of (meth)acrylic acid and co-monomers optionally contained is at least not less than 1:50 and at most 1:1, and (5) the ratio by weight of the outer phase to the inner phase is about 100:5 to 100:70.

The poly(meth)acrylic acid is intended to imply that the polymer is built up from acrylic acid and/or methacrylic acid as monomers. The cross-linking co-monomer, optionally used for the copolymerization, is a compound with two olefinic double bonds, particularly divinylbenzene, ethylene glycol di(meth)acrylate, diethylene glycol di(meth)acrylate or 1,4-butylene glycol di(meth)acrylate.

Furthermore, pursuant to the invention, the poly(meth)acrylic acid obtained can subsequently be cross-linked with a diglycidyl ether, preferably with butylene glycol diglycidyl ether.

The inventive poly(meth)acrylic acid dispersions are milky, cloudy to transparent, bluish to reddish, lustrous dispersions, which do not coagulate even after prolonged standing and, instead, have a high stability, and the color of which, after the temperature is raised to the boiling point of the oil phase, undergoes reversible changes from blue to red.

Of particular importance in this connection is the block copolymer used as stabilizer. This consists of at least one block A, which is formed by the polymerization of monomers containing vinyl groups such as, in particular, styrene, alkylstyrene or a methacrylate, and at least one block B, which is a polyoxyalkylene block. This block copolymer preferably corresponds to the A-B or A-B-A type. Admittedly, a block copolymer of the A-(B-A-) $_n$A type, in which n is a number greater than zero, can be used but offers no advantages over the block copolymer of the A-B or A-B-A type.

The molecular weight of this stabilizer, contained in the inventive dispersion, is about 1,000 to 20,000. Preferably, the ratio of the molecular weight of block A to the molecular weight of block B is about 0.5:1 to 9:1.

The polyoxyalkylene block B preferably consists of at least 70 mole percent of oxyethylene units, the remaining oxyalkylene units being those, in which the number of carbon atoms is greater than two. For example, block B can consist of 70 mole percent of oxyethylene units and 30 mole percent of oxypropylene units.

Preferably, however, block B contains oxyethylene units exclusively.

Particularly preferred are block copolymers of the A-B type, wherein block A is a polystyrene block and block B a polyoxyethylene block and the molecular weight of the stabilizer is about 1,000 to 6,000.

Block copolymers, particularly suitable as stabilizers, are described in the German patent 41 34 967. Block copolymers of the A-B type can be obtained by first of all polymerizing vinyl group-containing monomers in a known manner in the presence of adequate amounts of an initiator and a chain-length regulator, corresponding to the desired chain length. The chain-length regulator has, aside from mercapto groups, a further functional group having at least one active hydrogen. The polymerization is via free radical means at temperatures of 60° C. to 150° C., the polymer obtained is reacted, in the event that the functional group with one active hydrogen group is an OH or a COOH group, with alkali hydroxide or alkali alcoholate with removal of water or alcohol, and at temperatures of 20° C. to 180° C., alkylene oxide is added to the polymer, so modified, until the desired molecular weight of block B is attained. 1-Mercaptoethan-2-ol is an example of a chain-length regulator, which is particularly suitable for the synthesis and contains, aside from a mercapto group, a further group having at least one active hydrogen. These block copolymers are highly effective polymer surfactants.

A further essential distinguishing feature of the inventive poly(meth)acrylic acid dispersion consists therein that, for its preparation, the ratio by weight of the aforementioned stabilizer to the sum of (meth)acrylic acid and optionally contained monomers is about 1:3 to 1:100 and preferably 1:10 to 1:20.

The third distinguishing feature of the inventive poly(meth)acrylic acid dispersion consists therein that a costabilizer, which is water or an alkylene glycol with up to 3 carbon atoms, is used for its preparation. Examples of such alkylene glycols are 1,2-ethylene glycol and 1,3-propylene glycol. However, water is preferred as costabilizer.

Pursuant to a further distinguishing feature of the invention, it is of essential importance to maintain a particular ratio by weight of costabilizer, particularly water, to monomers, that is, to acrylic acid and/or methacrylic acid and optionally contained co-monomers. The ratio by weight of the costabilizer to the sum of (meth)acrylic acid and optionally contained co-monomers should be at least not less than 1:50 and at most 1:1. Preferably, water is used as costabilizer in a ratio by weight of water to methacrylic acid and optionally contained comonomers of not less than 1:20 to not more than 1:5. By maintaining this ratio by weight of costabilizer to monomers, it is ensured that the inventive poly(meth)acrylic acid dispersion has particles of the desired size of 20 to 300 nm.

Finally, the ratio by weight of outer to inner phase should be about 100:5 to 100:70.

The outer phase of the inventive poly(meth)acrylic acid dispersion is formed by a nonpolar, organic solvent. Of course, this statement is to be understood to imply that, in addition, the costabilizer and the stabilizer are contained in at least the essential amounts in the organic solvent. In particular and preferably, aromatic solvents or solvent mixtures and, in particular, those with a boiling point of not more than 150° C. are suitable as nonpolar organic solvents. It is particularly preferred if toluene forms the outer phase.

While maintaining the condition named above in relation to the selection of stabilizer and costabilizer and in relation to the quantitative relationships of stabilizer and costabilizer to the sum of (meth)acrylic acid and optionally contained co-monomers, the inventive poly(meth)acrylic acid dispersion is preferably prepared by (1) dissolving the stabilizer and the (meth)acrylic acid, optionally together with the co-monomers that are to be used, in the solvent,
(2) dissolving or dispersing the costabilizer in this solution,
(3) bubbling nitrogen through the solution,
(4) adding initiator, and then
(5) letting the polymerization, optionally proceed at an elevated temperature.

In the event that a cross-linking co-monomer is used, the latter can also be added at the end of the polymerization reaction and the cross-linking reaction can then carried out at higher temperatures of 60° C. to 100° C.

Particularly if the maximum permissible amounts of stabilizer, particularly water, in relation to the methacrylic acid is used, this method can initially result in an nonhomogeneous emulsion, which then however, in the course of the progressing polymerization, changes into the desired, milky, cloudy to transparent, lustrous colored dispersion.

The known, oil-soluble polymerization initiators, such as azobis(2,4-dimethyl-valeronitrile), can be used as initiators.

This general method of preparation can be modified by polymerizing initially only a portion of the (meth)acrylic acid and optionally the co-monomers in the presence of the total amount of costabilizer or also of only a portion hereof and adding, during or after the polymerization of this first portion, the remaining amount of (meth)acrylic acid and optionally the co-monomers, optionally with the remaining amount of the costabilizer and optionally in portions at intervals, and completing the polymerization. Further stabilizer and optionally costabilizer can subsequently be added within the given limits during the individual steps of the polymerization. A particularly narrow distribution of particles within the dispersion is achieved with this modified procedure.

The polymerization is carried out by this method at a high rate, which increases autocatalytically during the reaction.

Pursuant to the invention, poly(meth)acrylic acid dispersions are obtained with a particle size of 20 to 300 nm and, in particular, of 20 to 200 nm, this particle size distribution lying within narrow limits.

Upon warming, the inventive poly(meth)acrylic acid dispersions obtained show a reversible color change within a temperature interval from room temperature to the boiling point of the oil phase. When the dispersion is cooled, the original coloration reappears, so that these dispersions can be used as temperature indicators.

The inventive dispersions can be used as optical filter media. In view of their low particle size, the inventive dispersions are, however, exceptionally reactive modifiers for products, which are suitable for reacting with carboxyl groups.

It is, of course, readily possible, to those skilled in the art, to separate the poly(meth)acrylic acid particles from the dispersions and remove them from the organic phase and make further use of the polymer particles obtained. Especially preferred areas of application are the use of the polymer particles as superabsorbents, particularly in cosmetic or hygienic liquid-absorbing materials such as disposable diapers or as carriers for active ingredient depots, particularly in the pharmaceuticals area. The particles furthermore can form support materials for catalysts. They have a thickening effect in aqueous solutions, the extent of the thickening depends on the pH. They are furthermore suitable as chromatographic support materials.

The preparation of the inventive, finely particulate, polyacrylic acid dispersions is described in the following examples, it being understood that the Examples are provided by way of illustration and not by way of limitation.

EXAMPLE 1

In a reactor, equipped with a high-speed stirrer, 15 g of acrylic acid and 4 g of a polystyrene-polyoxyethylene block copolymer, in which the polystyrene block has a molecular weight of 3,000 and the polyoxyethylene block has a molecular weight of 1,000, are dissolved in 150 g of toluene and heated to 50° C. under nitrogen. At a stirrer speed of 400 rpm, 3 g of water are added, further nitrogen being passed through the solution. The polymerization is started by the addition of 0.2 g of azobis(2,4-dimethyl-valeronitrile). After a reaction lasting 20 minutes, 15 g of acrylic acid and 3 g of water are added once again. After a total reaction time of about 40 minutes, the reaction is completed.

After cooling to about 20° C., a blue, lustrous dispersion is obtained. The residual monomer content is not more than 0.5% by weight, based on the dispersion. The particle size is determined by light scattering and is about 110 nm.

By using a block copolymer of the A-B type of a polystyrene block and a polyoxyethylene block, wherein the polystyrene block has a molecular weight of about 1,000 and the polyoxyethylene block also has a molecular weight of about 1,000, particles with a diameter of about 160 nm are obtained.

By using a block copolymer, wherein the polystyrene block has a molecular weight of 3,000 and the polyoxyethylene block a molecular weight of 3,000, particles with a diameter of about 70 nm are obtained.

EXAMPLE 2

In a reactor, which is equipped with a high-speed stirrer, 20 g of acrylic acid and 1.1 g of a polystyrene-polyoxyethylene block copolymer, wherein the polystyrene block has a molecular weight of 3,000 and the polyoxyethylene block a molecular weight of 1,000, are dissolved in 150 g of toluene and heated to 50° C. under nitrogen. At a stirrer speed of 300 rpm, 2.3 g of water are added, further nitrogen being passed through the solution. The polymerization is started by the addition of 0.14 g of azobis(2,4-dimethyl-valeronitrile). After a reaction lasting 20 minutes, 20 g of acrylic acid, 2.3 g of water and 1.1 g of block copolymer are added once again and, after a further 15 minutes, 20 g of acrylic acid, 2.3 g of water and 1.1 g of block copolymer. After a total reaction time of 50 minutes, the polymerization is completed. Optionally, for cross-linking, 2.5 g of ethylene glycol diglycidyl ether can then be added, the reactor temperature simultaneously being increased to 60° C. to 70° C. The reaction time for the cross-linking is about 2 to 3 hours.

After cooling to 20° C., a yellowish, cloudy, violet irridescing dispersion is obtained. The particle size is about 170 nm.

We claim:

1. A (meth)acrylic acid polymer dispersion containing an inner phase and an outer phase obtained by free radical polymerization of (meth)acrylic acid in presence of a stabilizer, costabilizer and initiator and having an organic solvent as the outer phase, dispersed phase particles of average particle size of between about 20 and 300 nm and a low polydispersity, wherein
   (1) the stabilizer is a block copolymer consisting of at least one block A and at least one block B, block A being formed by polymerizing monomers containing vinyl groups and block B being a polyoxyalkylene block,
   (2) the ratio by weight of the stabilizer to the sum of (meth)acrylic acid and co-monomers optionally contained is 1:3 to 1:100,
   (3) the costabilizer is water or a dihydric alcohol with up to 3 carbon atoms,
   (4) the ratio by weight of costabilizer to the sum of (meth)acrylic acid and co-monomers optionally contained is at least not less than 1:50 and at most 1:1, and
   (5) the ratio by weight of the outer phase to the inner phase is about 100:5 to 100:70.

2. The poly(meth)acrylic acid polymer dispersion of claim 1, wherein the stabilizer is an A-B or A-B-A block copolymer.

3. The (meth)acrylic acid polymer dispersion of claim 1 or 2, wherein the ratio of the molecular weight of block A to block B is between about 0.5:1 and 9:1.

4. The (meth)acrylic acid polymer dispersion of claim 1 or 2, wherein the block A consists of at least 70 mole percent oxyethylene units and the remaining oxyalkylene units have greater than two carbon atoms.

5. The (meth)acrylic acid polymer dispersion of claim 1 or 2, wherein the ratio by weight of the stabilizer to the sum of (meth)acrylic acid and optionally contained co-monomers is between about 1:10 and 1 to 20.

6. The (meth)acrylic acid polymer dispersion of claim 1 or 2, wherein the costabilizer is water and the ratio by weight of water to the sum of (meth)acrylic acid and optionally contained co-monomers is not less than 1:20 to not more than 1:5.

7. The (meth)acrylic acid polymer dispersion of claim 1 or 2, wherein the outer phase is an aromatic solvent or solvent mixture with a boiling point of not more than 150° C.

8. The (meth)acrylic acid polymer dispersion of claim 1 or 2, wherein the outer phase contains toluene.

9. The (meth)acrylic acid polymer dispersion of claim 1 or 2, wherein divinylbenzene, ethylene glycol di(meth)acrylate, diethylene glycol di(meth)acrylate or 1,4-butylene glycol di(meth)acrylate is used as a cross-linking comonomer.

10. The (meth)acrylic acid polymer dispersion of claim 1 or 2, wherein the (meth)acrylic acid polymer obtained is subsequently cross-linked with a diglycidyl ether.

11. The (meth)acrylic acid polymer dispersion of claim 1 or 2, wherein butylene glycol diglycidyl ether is used for the subsequent cross-linking of (meth)acrylic acid polymer.

* * * * *